United States Patent
Ingle et al.

(10) Patent No.: US 8,821,484 B2
(45) Date of Patent: Sep. 2, 2014

(54) METHODS AND DEVICES FOR MONITORING TISSUE ABLATION

(75) Inventors: Frank Ingle, Palo Alto, CA (US); Joann Heberer, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 811 days.

(21) Appl. No.: 12/459,032

(22) Filed: Jun. 26, 2009

(65) Prior Publication Data

US 2009/0326526 A1 Dec. 31, 2009

Related U.S. Application Data

(60) Provisional application No. 61/129,467, filed on Jun. 27, 2008.

(51) Int. Cl.
*A61B 18/02* (2006.01)
*A61B 1/227* (2006.01)
*A61B 18/00* (2006.01)
*A61B 19/00* (2006.01)

(52) U.S. Cl.
CPC .............. *A61B 18/02* (2013.01); *A61B 1/2275* (2013.01); *A61B 2018/0022* (2013.01); *A61B 2019/464* (2013.01); *A61B 2018/0262* (2013.01); *A61B 18/0218* (2013.01); *A61B 2018/0212* (2013.01)
USPC .......................................................... 606/21

(58) Field of Classification Search
USPC .......................................... 606/20–27, 34, 41
See application file for complete search history.

(56) References Cited

U.S. PATENT DOCUMENTS

| | | | |
|---|---|---|---|
| 5,312,401 A * | 5/1994 | Newton et al. .................. | 606/46 |
| 2001/0021849 A1 | 9/2001 | Swartz | |
| 2002/0087156 A1 * | 7/2002 | Maguire et al. ................. | 606/41 |
| 2006/0069385 A1 * | 3/2006 | Lafontaine et al. ............. | 606/21 |

FOREIGN PATENT DOCUMENTS

| EP | 0 856 326 A1 | 8/1998 |
|---|---|---|
| WO | WO 00/51511 | 9/2000 |

OTHER PUBLICATIONS

International Search Report and The Written Opinion of the International Searching Authority, or the Declaration; International Application No. PCT/US 2009/048820; International Filing Date Jun. 26, 2009; 15 pgs.

\* cited by examiner

*Primary Examiner* — Michael Peffley
*Assistant Examiner* — Daniel Fowler
(74) *Attorney, Agent, or Firm* — Seager, Tufte & Wickhem, LLC

(57) ABSTRACT

A method, system, and device for detecting whether an expandable member completely occludes an anatomic passageway allows a user, such as a physician, clinician, or surgeon, to perform a medical procedure more efficiently and increases the procedure's chances of success. An incomplete occlusion can be immediately detected by monitoring the pressure difference across the expandable member. Through this method, a user can quickly diagnose the problem and reposition the expandable member in the anatomic passageway. In particular, in a cryoablation procedure, devices incorporating this method can help ensure a uniform and complete lesion in the pulmonary vein to electrically isolate the pulmonary vein from the atrium, thus preventing atrial fibrillation.

24 Claims, 7 Drawing Sheets

METHODS AND DEVICES FOR MONITORING TISSUE ABLATION

CROSS REFERENCE TO RELATED APPLICATIONS

This application claims priority to Provisional Application Ser. No. 61/129,467, entitled "Methods and Devices for Monitoring Tissue Ablation," filed Jun. 27, 2008.

BACKGROUND

Atrial fibrillation is an irregular heart rhythm that adversely affects approximately 2.5 million people in the United States. It is believed that at least one-third of all atrial fibrillation originates near the ostium of the pulmonary veins. Anatomically, two pairs of pulmonary veins are connected to the left atrium of the heart with each pair delivering blood to the heart from one of a patient's lungs. Accordingly, one technique to treat atrial fibrillation includes the formation of circumferential lesions around the ostia where a pulmonary vein connects with the left atrium. Forming a conduction block, via tissue ablation, can inhibit the transmission of irregular electrical signals responsible for inducing an arrhythmia. However, to be most effective, a relatively deep, uniform lesion is preferred.

Cryoablation is one method for creating the circumferential lesions that block the conduction of irregular signals through the pulmonary vein. In one type of cryoablation procedure, a balloon is positioned within the ostia of the pulmonary vein, thereby creating a seal. The balloon may contain an ablation fluid that is gaseous or liquid, such as saline, nitrous oxide, or perfluorocarbon. Typically, the ablation fluid cools tissue in contact with the outer surface of the balloon to a temperature that destroys cells. This disables the transmission of the irregular signals responsible for atrial fibrillation. It should also be noted that cryoablation procedures can treat other conditions such as stenosis.

Another type of cryoablation procedure involves treating the ostium tissue with a separate cryoablation member located outside the balloon. The cryoablation member can freeze the tissue by directly touching the tissue or by spraying the tissue with a coolant, depending on the approach.

While such procedures have proven effective, further improvements, particularly regarding positioning of ablation devices relative to an anatomic structure, would be beneficial.

SUMMARY

In accordance with an embodiment herein, a system and method allows a user to monitor a seal formed between a cryosurgical balloon and tissue by monitoring relative and/or absolute pressures at spaced locations with respect to an anatomic passageway. In one aspect, pressure sensors associated with a cryoablation device measure pressure on opposite sides of an expanded balloon to determine if the balloon forms a seal that sufficiently or completely occludes the anatomic passageway. For the purposes of this disclosure, a complete occlusion occurs when the occlusion is sufficient to provide a lesion with enough uniformity to lead to a successful procedure. When the seal is functionally intact, a comparison between the sensors reveals a difference in pressure. If substantially no pressure difference is detected, then the seal contains a leak and the occlusion is incomplete. This difference in pressure may be presented to the user visually, such as on a monitor, and/or aurally, such as via alarm(s) or prerecorded messages.

Additional objects and advantages of the embodiments will be set forth in part in the description that follows, and in part will be obvious from the description, or may be learned by practice of the embodiments. The objects and advantages of the invention will be realized and attained by means of the elements and combinations particularly pointed out in the appended claims.

It is to be understood that both the foregoing general description and the following detailed description are exemplary and explanatory only and are not restrictive of the embodiments, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF EXEMPLARY EMBODIMENTS

Reference will now be made in detail to the present exemplary embodiments, examples of which are illustrated in the accompanying drawings. Wherever possible, the same reference numbers will be used throughout the drawings to refer to the same or like parts.

Blood flow can be blocked from interfering with an ablation procedure by maintaining a seal that completely or substantially occludes blood flow through an anatomic passageway, such as a pulmonary vein. In one embodiment described herein, the occlusion seal is formed by placing an expandable device within the ostia region of the pulmonary vein. Proper positioning of the expandable device and/or formation of a seal can be confirmed by monitoring the relative pressure on each side of the seal. This allows a clinician to remedy any break in the occlusion seal and can permit formation of a more uniform circumferential lesion without the need to repeat the procedure or perform a time-consuming point-to-point ablation.

While cryoablation in the pulmonary vein is described specifically herein, one skilled in the art will appreciate that the methods and device provide can be adapted for use in, or proximate to, other anatomic or non-anatomic structures. Moreover, the devices described herein need not perform cryoablation. While cryoablation is described in detail, other ablation procedures, such as for example, radio-frequency and microwave-type ablation could be used with the expandable device. Further, ablation devices could be additionally or alternatively located on a device or system separate from the occluding devices illustrated herein and/or the devices described herein could be used in procedures that do not include an ablation step.

Figure 1:
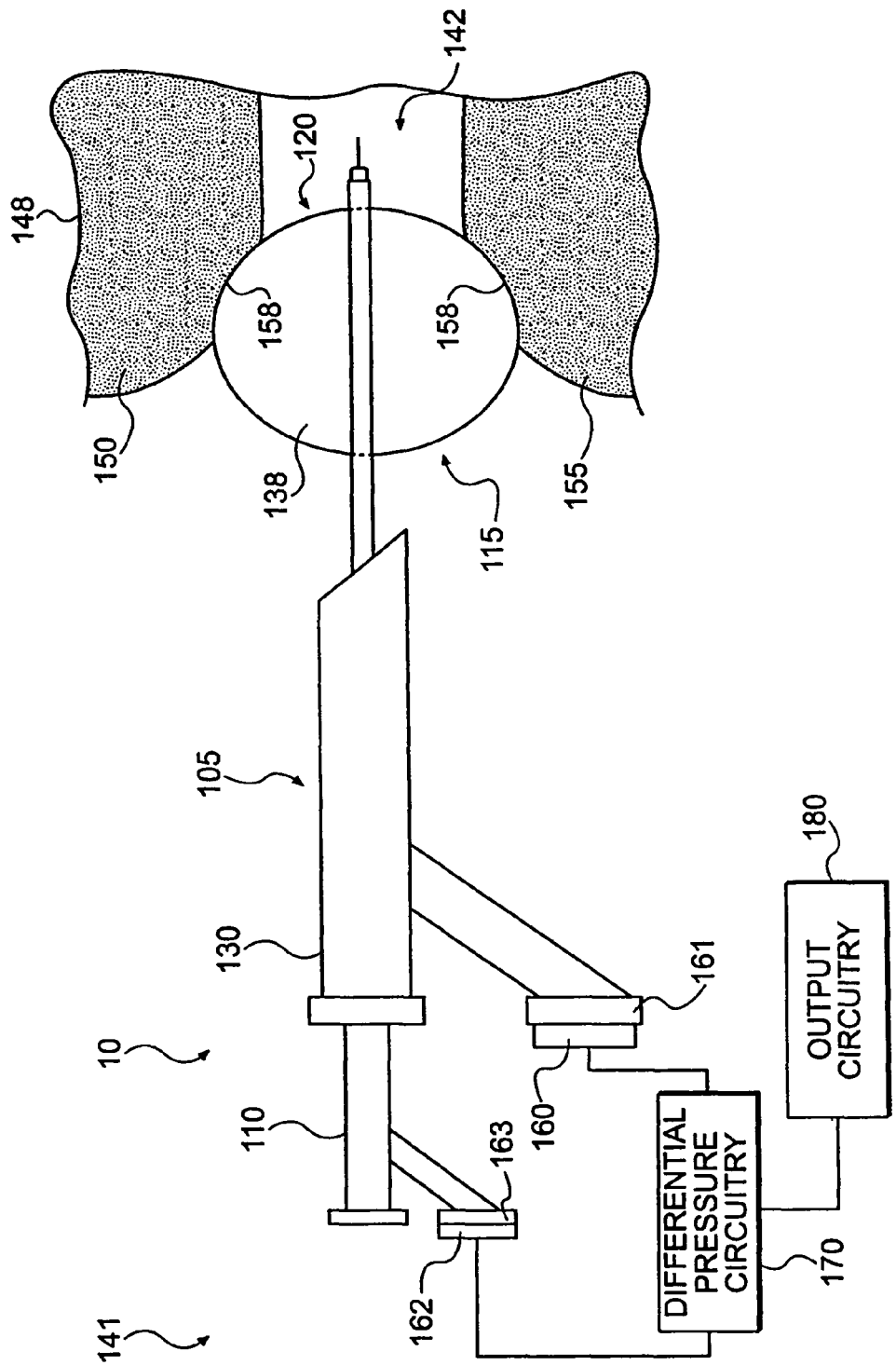
FIG. 1 is an exemplary longitudinal view of one embodiment of a medical device described herein for performing an ablation procedure.

FIG. 1 is an exemplary side view of a device 10 for performing a cryoablation procedure in accordance with one embodiment. Generally, device 10 includes an elongate body 105 (also referred to herein as a catheter body) extending between a proximal end 141 and a distal end 142. The elongate body 105 can include an expandable member 138 for at least partially occluding an anatomic structure. In one aspect, expandable member 138 is positioned proximate to the distal end of elongate body 105.

Expandable member 138 can include a variety of structures configured to expand in cross-section from a first insertion configuration to a second, larger, occluding configuration. During insertion of device 10, expandable member 138 can have a first size and shape that allows insertion through vasculature. Upon reaching a target tissue location, the expandable member can be expanded to seat the device at a desired location relative to the target tissue.

In one aspect, expandable member 138 is an inflatable device that can be expanded, for example, by infusion with a fluid. The expandable member 138 can be formed from a variety of flexible, deformable, and/or stretchable materials that permit expansion, including, for example, medical grade polymers and elastomers. However, the expandable member need not be stretchable. For instance, the expandable member can be folded and can unfold to expand and increase in size. In use, the materials forming the expandable member can limit or control maximum expansion and reduce the chance of applying excessive pressure on sensitive tissue surfaces. Alternatively, the expandable member can be a balloon-like structure that stretches or deforms to permit volume expansion.

Regardless of the materials used to form the expandable member 138, the expandable member 138 can be defined by one or more bodies (having the same, similar, or different properties) and can include one or more chambers. In one aspect, the expandable member can include a first and second chamber defined by first and second expandable bodies. In particular, one of the chambers can receive a cryo-fluid while the other chamber expands to occlude a vessel and/or to position the first chamber. Examples include concentrically arranged and side-by-side expandable bodies. In addition, multiple ablation chambers can be positioned within the expandable member to permit patterning or segmented ablation. In still another aspect, multiple expandable members can be used with the systems and device described herein. One skilled in the art will appreciate that a variety of expandable member structures are contemplated and the expandable member can be varied depending, for example, on the type of ablation and/or target tissue location.

The expandable member 138 can also comprise a balloon structure. The balloon can have a substantially circularly shaped cross-section in a plane substantially orthogonal to the longitudinal axis of the balloon catheter. However, the balloon shape can vary to accommodate the target tissue area. The balloon can also be compliant such that when the balloon contacts the target tissue structure, the tissue surface can shape the balloon into a corresponding configuration. In addition, or alternatively, the balloon can compress or deflect tissue to change the shape of the target tissue.

In addition to the above inflatable members, other expandable member 138 structures are also contemplated. For example, mechanically expandable structures can be used in association with the methods described herein. One such example is the use of mechanical arms to drive expansion of an expandable structure. In another aspect, flaps positioned around elongate body 105 can be pivoted or rotated into position to mate device 10 with tissue and/or occlude a vessel.

Regardless of the configuration of the expandable structure 138, the size and shape of expanded structure can correspond in side and/or shape to a target tissue region. Thus, a variety of expanded shapes and sizes are contemplated depending on the use of device 10. In one aspect, the expandable structure has a generally spherical shape. However, a variety of other geometric or irregular shapes could be substituted.

In one embodiment, the expandable body is mated with a distal portion of the catheter body and the catheter body can house at least one lumen for the delivery of an inflation medium to the expandable body. However, the expandable body and catheter body need not be fixedly mated and in one aspect, the expandable body can be inserted separately from the catheter. For example, the expandable body can be inserted through a catheter body and expanded through an opening in the catheter body. Regardless, the catheter body can be associated with more than one expandable member and/or an expandable member can be associated with multiple catheter bodies.

Catheter body 105 includes at least one lumen or channel, and can include two, three or more separate channels that extend over all or a portion of the length of the catheter. In one aspect, the catheter body can include one or more lumens or channels that define fluid pathways, house wires for transmitting/receiving signals, and/or include actuating mechanisms for controlling movement of a portion of the catheter.

In the illustrated embodiment, the expandable member 138 is mated with the catheter body 105 proximal to the distal-most end of the catheter such that the expandable member expands radially from the longitudinal axis of the catheter. Alternatively, multiple expandable members could be positioned around the catheter body and/or an expandable member could be expanded from one side of the catheter body. In other words, the expandable body and catheter need not have a concentric or coaxial configuration.

The distal tip of the catheter can include a blunt surface to assist with insertion of device 10 and to minimize tissue trauma. In addition, or alternatively, the tip, or a portion of the catheter proximate to the distal tip can include an opening for the delivery of a therapeutic substance and/or medical instrument.

The size and shape of catheter body 105 can be chosen based on the intended use of device 10. Where device 10 is used for cardiac ablation, catheter 105 can be sized and shaped for insertion through a vascular lumen. In addition, the materials and structure of catheter can be chosen to provide a flexible elongate body. One skilled in the art will appreciate that body 105 can represent the variety of catheter structure commonly known in the art for a vascular approach.

The proximal end of device 10 can include a user interface or handle that permits a clinician to grasp device 10. The handle can have a variety of forms depending on the intended use of device 10 and/or the environment in which device 10 is used. In one aspect, the handle can include one or more sources of liquid or gas for expanding expandable member 138. The liquid can be a cryo-fluid or volume displacement fluid. Controls for governing the delivery of the liquid or gas can, in one aspect, also be located on the handle. Alternatively, or additionally, the proximal portion of catheter 105 can be configured to mate with one or more sources of liquid. In one embodiment, the fluid source includes a cryo-fluid and/or volume displacement fluid and can further include a mechanism for regulating and controlling expansion of expandable member 138 via delivery of fluid. In yet another aspect, the catheter body can include one or port ports for receiving or removing fluid, biological samples, therapeutic agents, instruments, and/or other related devices and materials.

After the expandable member 138 is successfully placed within the anatomic structure, cryoablation can be performed. In one embodiment, such as in FIG. 1, expandable structure 138 is cooled to a temperature that destroys cells along the walls of an anatomic passageway, such as pulmonary vein 148, to some depth. The balloon 138 may be filled with an ablation fluid (e.g., a gas or fluid) including the variety of known substances for cryoablation procedures, examples of which include saline solution, perfluorocarbon, nitrous oxide, and combinations thereof. Typically, the ablation fluid is cryofluid or coolant. The cryofluid can be introduced into the balloon from the proximal side of the catheter in one implementation. In one embodiment, the coolant is used to inflate the expandable body at least in part. A lumen can also be provided to expel used coolant and/or create a flow of cooling fluid through the expandable member.

Alternatively, the expandable member 138 may be heated to a temperature that kills surrounding cells. In a heat-based embodiment, the expandable member 138 can surround a heat source positioned within the expandable member 138 and/or a heating fluid can be delivered into device 10. In addition, the heating can be effectuated by radiation or conduction from a point inside the expandable member 138. A separate radiation member can be located inside the balloon 138. The expandable member 138 can be used to control the shape of the radiation or conduction. Consequently, the balloon 138 may come in a variety of shapes depending on the exact procedure being performed and the ablation shape and/or pattern required.

The cryo-catheter can include a supply lumen for delivery of ablation fluid to the expandable member. In one implementation, a return tube is positioned inside the lumen of the cryo-catheter to establish a return line. In this way, the ablation fluid may be provided through the supply lumen and, after the substance has been used, returned through the supply tube. In one embodiment, a supply of hot or cold ablation fluid is circulated through the expandable member, and stirring may be provided.

A supply tube need not be directed through the interior of the catheter in one embodiment. For example, some other path to the site of the procedure is possible. Likewise, the return tube is not directed through the interior of the catheter in all embodiments.

With reference to FIG. 1, the catheter body can be defined by one or more segments fixedly, movably, and/or detachable mated within one another. In one aspect, an outer sheath 130 extends along at least a portion of the outer surface of an inner sheath 110 containing a coolant supply lumen. The sheath 130 can inhibit unintended freezing of any tissue, blood, and/or other biological substance contacted by the cryo-catheter and/or supply lumen during distribution of the coolant.

In one aspect, the expandable member can be movably mated with catheter 105. For example, the system can include a slidable part, such as a cylindrical-shaped sleeve, for use in positioning a balloon at the treatment site. In greater detail, the expandable member can be mounted on the sleeve. The sleeve may then be mounted over the cryo-catheter or some other guide wire that leads to the desired site of the procedure. The system further can include a fill tube attached to the sleeve to fluidly communicate with the expandable member.

In another embodiment, the expandable member is separate from the ablating structure. For example, expandable structure 138 can act as an occluding device while a different structure effects ablation. In one such embodiment, a cryoablation member positioned distally to the expandable member sprays a liquid coolant directly onto the walls of the anatomic passageway. In one aspect, the cryoablation member can be delivered through a lumen defined by catheter 105. Alternatively, the cryoablation member can be mated with catheter 105 and cryo-fluid can be delivered through catheter 105 to the cryoablation member.

In any embodiment, occlusion can facilitate the formation of a uniform circumferential lesion. As shown in FIG. 1, an occlusion seal 158 is formed when the pulmonary vein is sealed with the expandable member. The seal helps ensure that the circumferential lesion caused by cryoablation is uniform, and properly blocks problematic electrical impulses from passing to the atrium. For example, if the expandable member 138 is responsible for ablating the tissue, an unclosed gap between the expandable member 138 and tissue (e.g., tissue region 150 or 155) can result in a non-uniform circumferential lesion because of non-uniform heat or energy transfer between the expandable member and tissue.

Figure 2:
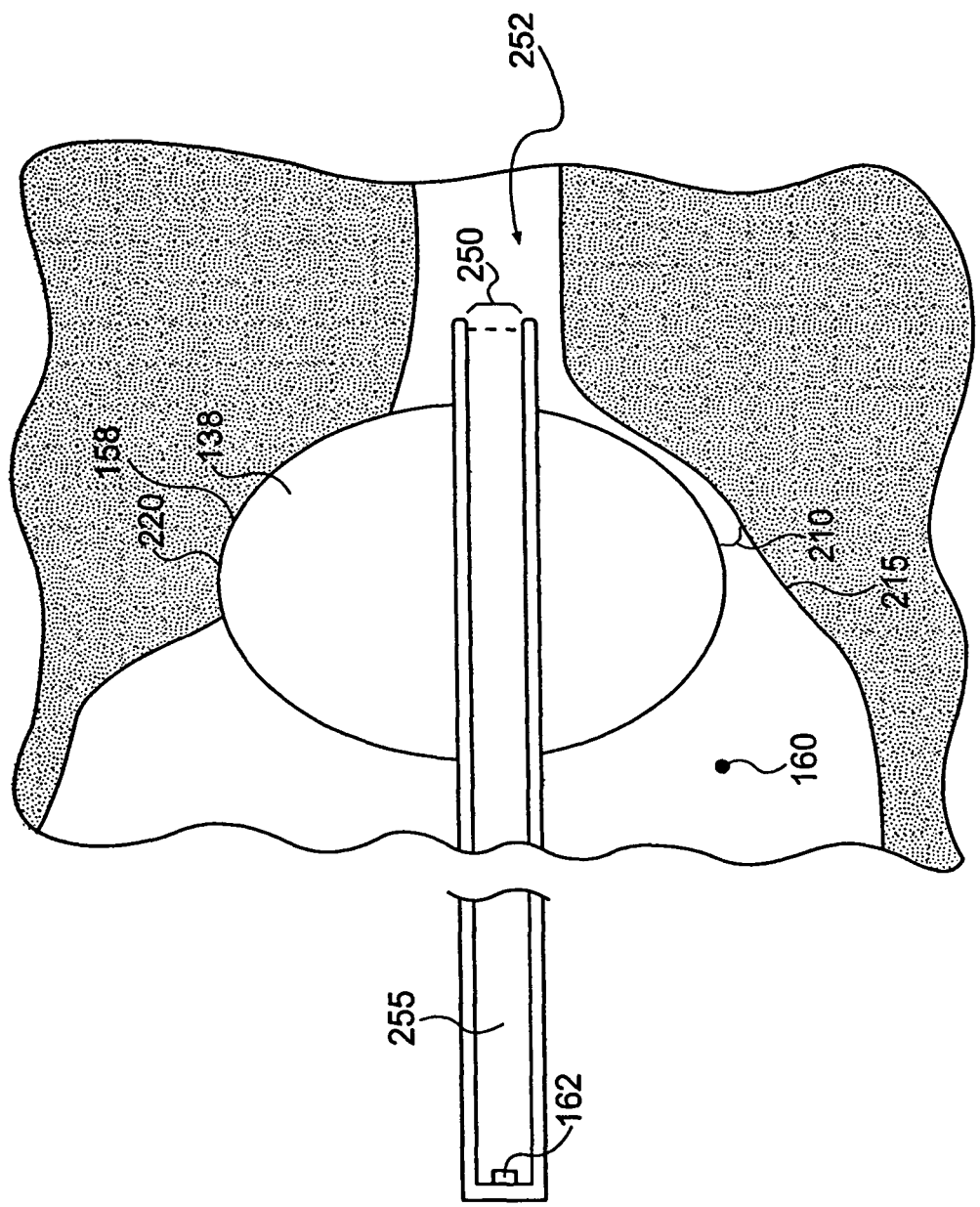
FIG. 2 is an exemplary longitudinal, cross-sectional view of an ablation device partially occluding an anatomic structure.

Turning to FIG. 2, a gap 210 is illustrated between tissue surface 215 and balloon 138. Because the balloon 138 is pressed firmly against tissue surface 220, the ablation procedure can destroy tissue at 220 more effectively than at 215. The gap and/or blood flowing through gap 210 can insulate tissue 215 and interfere with effective heat transfer between balloon 138 and tissue 215. For example, the blood flow can counteract the heating or cooling of the tissue 215 by absorbing the heat or cooling effect as it washes past surface 215.

Gap 210 may be acceptable or have minimal impact on the ablation procedure. For example, an ice layer (e.g., ice ball) may form on the outside of the balloon 138 that effectively fills the gap 210. In this way, even though separation exists between the balloon 138 and the tissue 220, the pulmonary vein can remain completely occluded. As described in more detail below, the device and systems described herein can, in one aspect, detect If the gap 210 is filled with ice sealing the pulmonary vein.

In general, however, the presence of gap 210 can hinder the ablation procedure, and result in a shallower lesion or non-uniform circumferential lesion in the pulmonary vein. A non-uniform lesion might not block impulses from passing into the atrium, and consequently the procedure fails to prevent future atrial fibrillations. In some instances, it is difficult to determine the long-term effectiveness of the lesion until after the cryoablation procedure is complete. Therefore, it is helpful if the occlusion is as complete as possible during ablation to help ensure that the lesion is uniform.

The presence of a seal in the anatomic passageway (or lack thereof) can be detected by measuring a pressure drop at spaced proximal and distal locations. In one embodiment, pressure is measured on either side of the expected location of seal 158. A first pressure can be detected at a location proximate to a distal surface of expandable structure 138 and inside the pulmonary vein. The first pressure is compared to a second pressure detected proximate to a proximal surface of expandable structure 138 located inside the atria. In one embodiment, the first and second pressures are measured at locations that can detect the pressure drop from the pulmonary vein to the atrium.

Stated another way, the first and second sensors can measure pressure on either side of the location at which the expandable member contacts tissue. The first pressure can be measured distal to the contact area and the second pressure can be measured proximal to the contact area.

In one aspect, sensors positioned in a proximal portion of catheter body 105 can sense pressure distal to the expandable member. In FIG. 2, a hollow lumen 255 contains an opening 250 on the distal side of balloon 138. A sensor 162 located within lumen 255 at the proximal side of balloon 138 can measure the pressure on the distal side of balloon 138. Measuring a distal pressure with sensor 162 located at the proximal side of balloon 138 can reduce bulkiness at the distal end 252 of the medical device.

Figure 3:
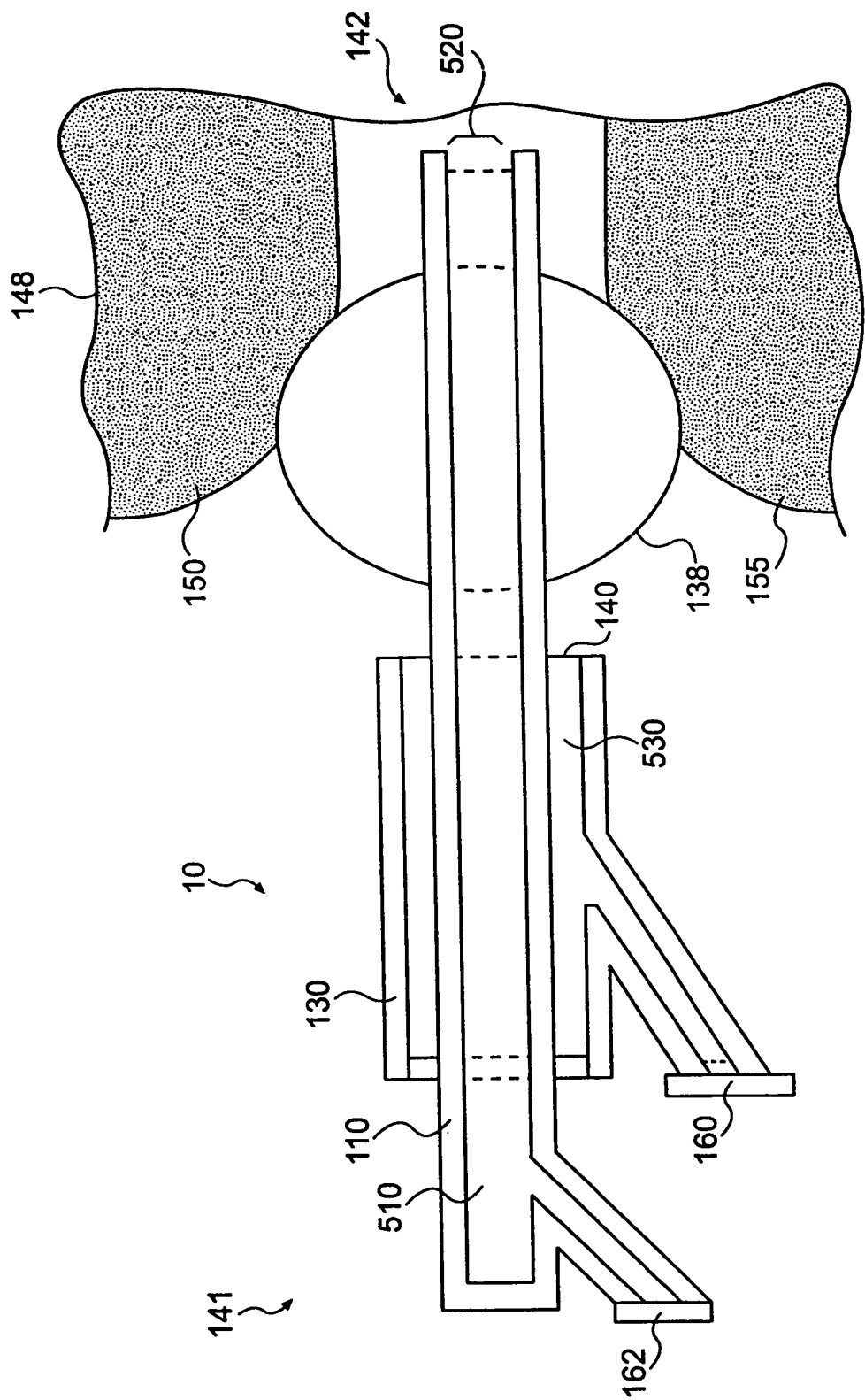
FIG. 3 is an exemplary longitudinal, cross-sectional view of a medical device for performing a cryoablation procedure in accordance with an embodiment herein.

FIG. 3 depicts an exemplary longitudinal, cross-sectional view of a medical device including a lumen 510 defined by the inner sheath 110. The inner sheath 110 can be a catheter in one embodiment. Lumen 510 can extend between a proximal end 141 of device 10 and opening 520 distal to the distal side of balloon 138. Lumen 510 can be fluidly sealed from the surrounding environment proximal to balloon 138 such that the pressure at the proximal end of lumen 510 equalizes with pressure in the anatomic chamber distal to balloon 138. Thus, the distal pressure can be measured at the proximal side of the balloon 138 via first sensor 162. A second sensor 160 can measure the pressure proximal to balloon 138.

In one aspect, a channel 530 is defined by a space between the outer surface of inner sheath 110 and the inner surface of outer sheath 130. The second sensor 160 can sense pressure proximal to the location where balloon 138 contacts tissue and/or proximal to the proximal surface of balloon 138. As illustrated in FIG. 3, an opening 140 at the distal end of channel 530 allows second sensor 160 to measure pressure proximate to balloon 138 from a proximally spaced location. In another embodiment, the second pressure sensor 160 is located outside the medical device and measures the fluid column pressure of lumen 530 from outside the patient.

In one aspect, the second pressure sensor 160 may provide a pressure value against which the first pressure sensor value can be measured. For example, the second differential pressure sensor may be calibrated to output a pressure relative to ambient atmosphere pressure. In one such embodiment, the pressure difference is therefore the pulmonary vein pressure, as sensed by the first sensor relative to the pressure value of the second sensor.

While FIGS. 1 and 3 illustrate device 10 having concentric sheaths 110, 130, a variety of alternative configurations are contemplated. For example, parallel lumens could extend to openings 520 and 140, respectively.

Figure 4:
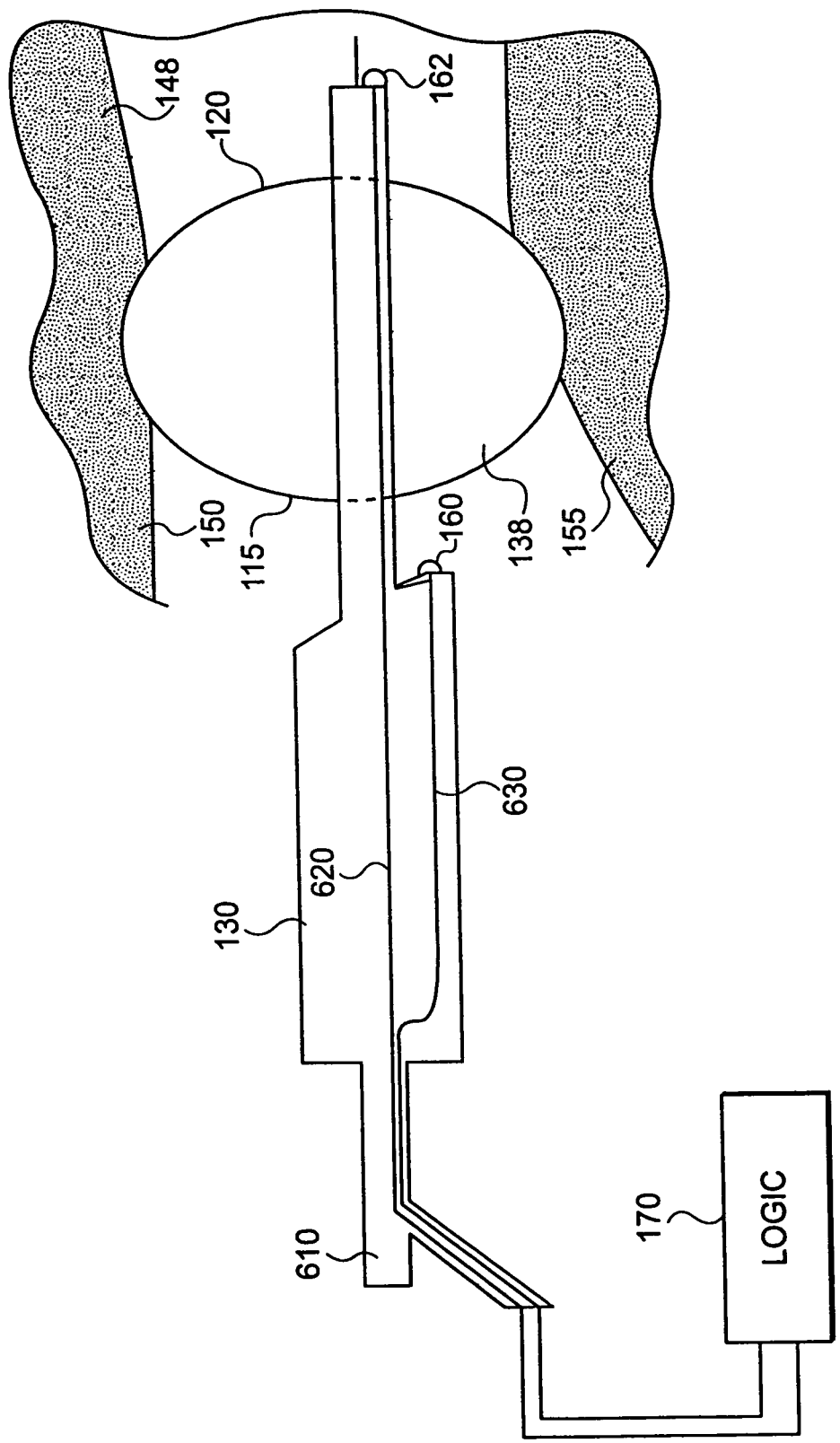
FIG. 4 is an exemplary longitudinal view of a medical device for performing a cryoablation procedure in accordance with another embodiment herein.

In yet another embodiment, an example of which is shown in FIG. 4, first pressure sensor 162 is positioned on the distal side 120 of balloon 138, while second pressure sensor 160 is positioned on the proximal side 115 of the balloon 138. In this embodiment, the lumen or catheter 610 may contain conductive paths 620 and 630 for receiving signals from pressure sensors 162 and 160, respectively. Conductive paths 620 and 630 can be in communication with sensors 162 and 160 and with logic 170 for analyzing the detected pressure differences.

Figure 5:
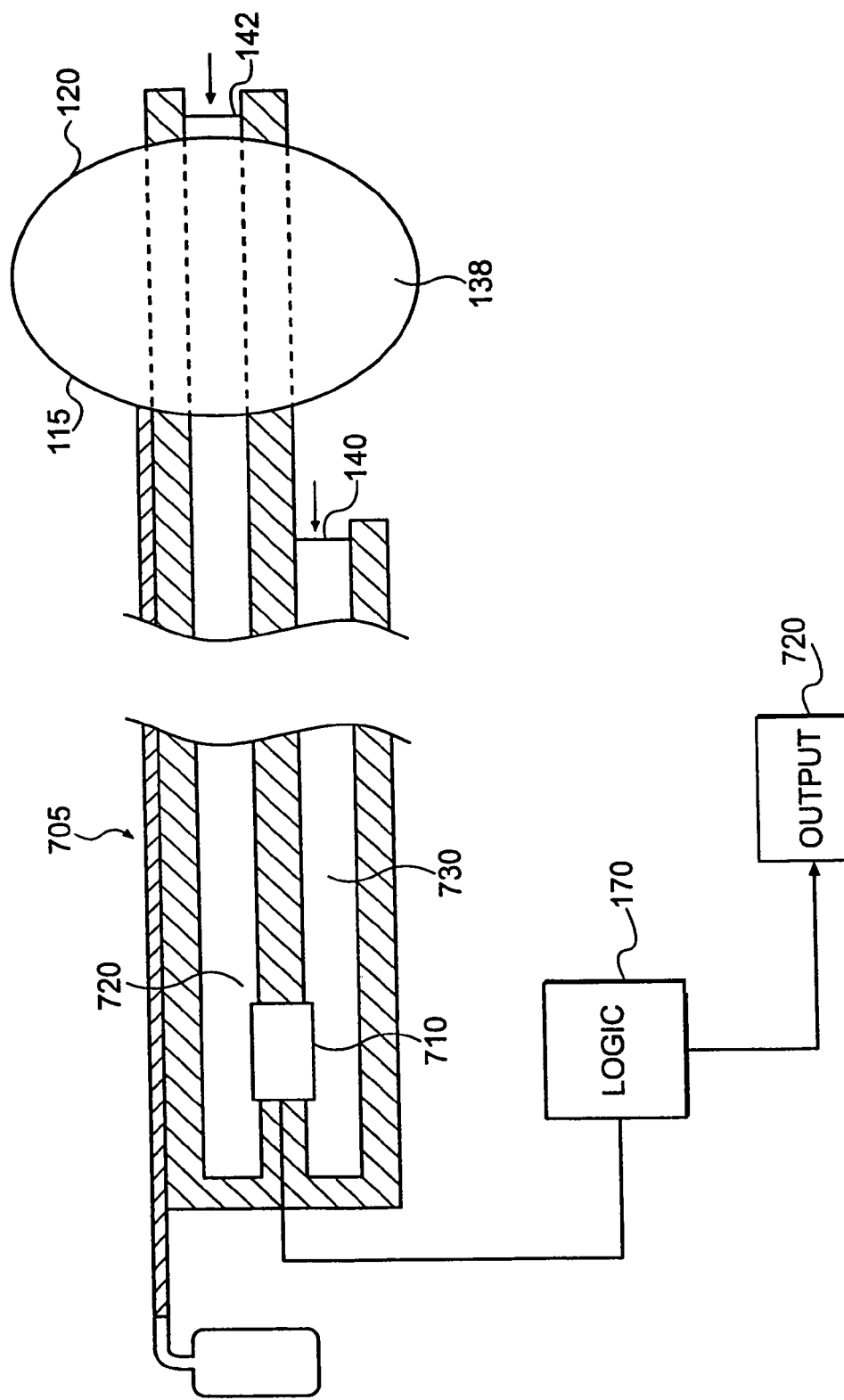
FIG. 5 is an exemplary longitudinal, cross-sectional view of a medical device for performing a cryoablation procedure in accordance with yet another embodiment herein

FIG. 5 is an exemplary illustration of still another embodiment, wherein a catheter 705 incorporates a single differential sensor 710 to measure the pressure difference between the proximal 115 and distal 120 sides of balloon 138. In this embodiment, differential sensor 710 is positioned between paths 720 and 730. Path 720 can extend to an opening beyond balloon 138, while path 730 can extend to an opening proximal to balloon 138. The differential pressure measured via sensor 710 can be communicated to logic 170 and/or output as a visual and/or aural response to the user through output 720.

Regardless of the pressure sensor configuration, the first pressure can be compared to the second pressure based on signals received from pressure sensors. In one aspect, two or more pressure readings are displayed for a user and the user can compare the sensor readings to confirm proper placement of the expandable structure and that a seals has been established.

Alternatively, a differential pressure circuitry 170 can compare pressure readings. In one embodiment, the pressure sensing circuitry 170 incorporates digital circuitry for analyzing the pressure difference. The digital circuitry can incorporate logic gates and/or a microprocessor. In another embodiment, the pressure-sensing circuitry 170 includes analog components. An amplifier may be used to amplify the pressure signal(s) for analysis purposes, and other circuitry may be used to communicate the pressure drop (or lack thereof) to a user, as discussed below.

In one embodiment, the differential pressure circuitry 170 is incorporated into the medical device 105. For example, the circuitry can be mounted within a housing or handle. In one embodiment, the differential pressure circuitry 170 remains external to the patient, and can even be external to the catheter in one aspect. For example, wires may connect the differential pressure circuitry 170 to the catheter. In another embodiment, a wireless transmission between the catheter and the differential pressure circuitry may occur.

Figure 6:
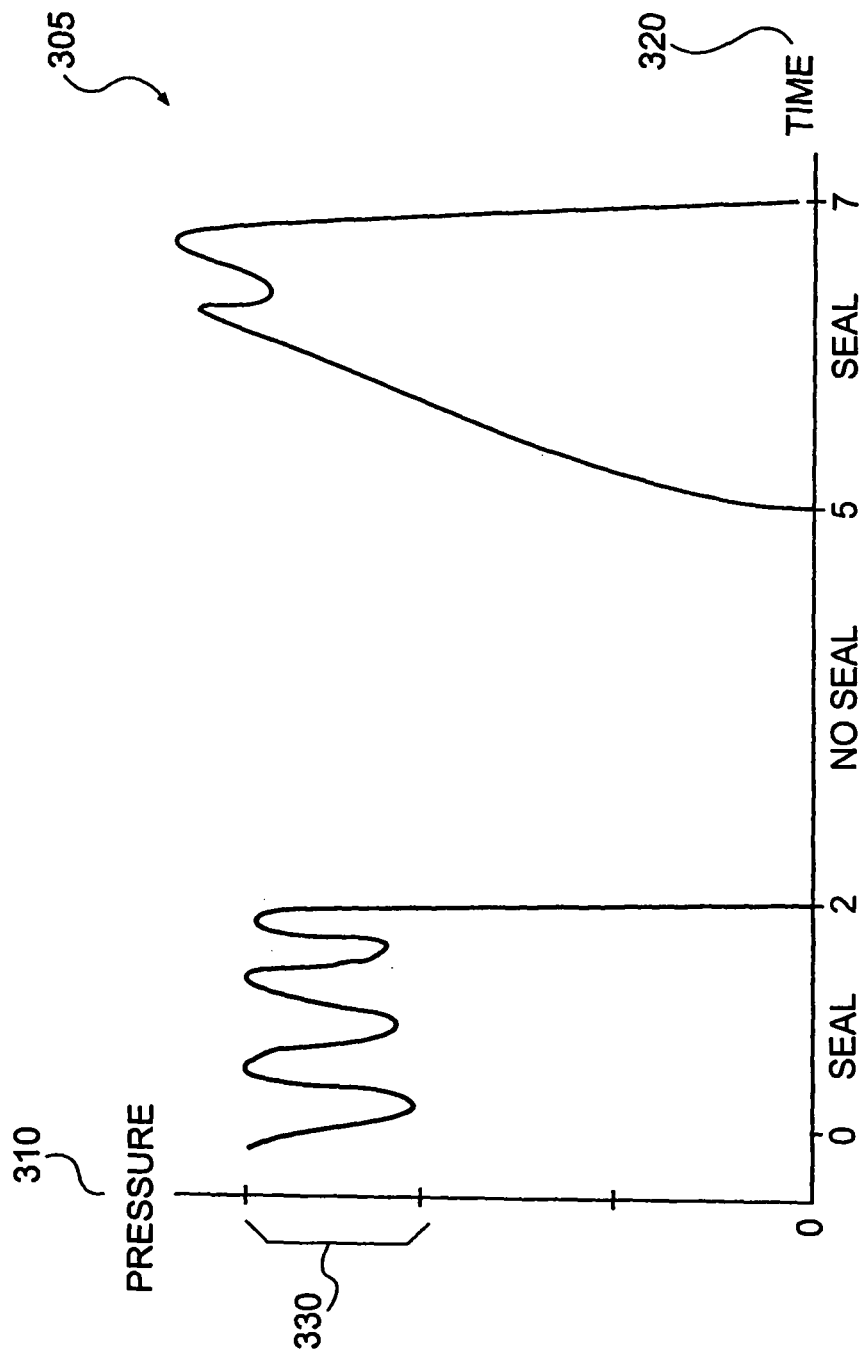
FIG. 6 is an exemplary illustration of a pressure difference display in accordance with one embodiment.

Pressure differential can be displayed in a variety of ways. In one embodiment, as shown in FIG. 6, the pressure differences are plotted on a display as a graph 305 of pressure difference 310 versus time 320. In this example, the pressure indicates that a complete occlusion (i.e., seal) exists when the pressure is within a predetermined range 330. Between time 0 and time 2, a seal is present. But at time 2, the seal is lost and is not regained until time 5. As illustrated, in one embodiment the pressure difference does not instantaneously fall into the predetermined range 300 upon occlusion, but instead first ramps up towards the predetermined range 330. An embodiment that graphs the pressure difference can also provide historical data for gauging the success of an ablation procedure. For instance, the physician or surgeon may be shown the length of time that passed during which the occlusion was incomplete, and adjust the ablation procedure accordingly. The display screen can also include other readings, such as a pressure reading inside the balloon. Tracking additional readings along with the pressure drop across the balloon 138 could help the user understand why complete occlusion was lost, and make appropriate adjustments.

In another embodiment, the output 720 includes an aural component, such as an alarm, that alerts the user when pressure readings indicate that the seal is broken. When the seal is reformed, the alarm stops sounding in one embodiment. In one instance, the alarm is a human voice that warns that the seal is broken and/or notifies the user when the seal is complete. The aural component may aid the user in quickly fixing the incomplete occlusion, such as when the user is not looking at the display 180 (FIG. 1). Additionally, or alternatively, notification of when occlusion is complete can help the user initially form the seal in the anatomic passageway. When the user hears the aural indicator, the user may then begin the ablation procedure, knowing that a seal is in place. The aural indicator may also have a pitch or loudness that varies proportional to the pressure difference across the balloon.

A pressure difference of approximately zero between the proximal and distal sides of balloon 138 indicates that the anatomic passageway is not occluded, and the seal is not present. In this case, the user should adjust the balloon 138 to reform the seal in order to ensure a successful ablation procedure, such as by adding additional inflation fluid. Adjustment may be performed, for example, by repositioning the balloon and/or adjusting the pressure inside the balloon (e.g., by further inflating the balloon) until the occlusion is once again complete.

The differential pressure range representative of a complete occlusion can vary depending on the placement of the sensors and/or the anatomic passageway being occluded, the expected or measured blood pressure adjacent to the location of the implanted expandable structure, and/or the need to form an absolute occlusion. In the case of a pulmonary vein, the pressure difference indicative of a complete occlusion can be between about 10 mm Hg to about 50 mm Hg. In another embodiment, the difference is between about 30 mm Hg to about 40 mm Hg. However, this range can vary depending on the characteristics of the individual heart. As is shown in FIG. 6, the pressure can vary upwards and downwards within the range 330 that indicates complete occlusion. This variance can be caused, for example, by the beating of the heart. Additionally, the heart rate and forcefulness of heart contractions can affect the pressure drop. Other physiological activity, such as breathing or muscle movement, can also produce slight variation in the pressure readings.

In addition, when graphing the pressure difference versus time, a slight delay in actual versus sensed pressure can exist, depending on the length and mechanical compliance of the catheter tubing (e.g., lumens). As a result of the compliance, a pressure change at the distal end of the catheter might not be immediately apparent at the proximal end of the catheter. However, the time delay, if present, can be indicated to the user or its impact reduce with a predictive algorithm in one embodiment.

In one embodiment a user can program the threshold range at which the device will notifies the user that occlusion is complete and/or that no seal is present. This allows the user, such as a physician, to set the range specifically for an individual patient, particularly patients whose pressure characteristics at complete occlusion do not fall within the typical pressure range. In one embodiment, the user can program an upper and lower pressure threshold. A differential pressure above the upper threshold indicates the existence of a seal. After a seal is present, the pressure must drop below the lower threshold before a break in the seal is indicated in that embodiment. In some embodiments, the lower threshold is near zero mm Hg. However, the pressure range might be influenced by factors already mentioned, including the size of the heart and/or pulmonary vein. In addition, an indication of occlusion in other anatomic passageways might involve widely different pressure drops across the balloon, for which programming may be needed.

As another option, the physician can set a time offset before the aural component alerts the physician regarding a break in the seal in an embodiment. This offset can help eliminate unwarranted alarms when the pressure momentarily dips below or rises above the pressure thresholds as a natural occurrence not indicative of an incomplete occlusion.

These settings and features can be accessed and adjusted through an input interface in one embodiment. The interface can include a mouse, keyboard, voice recognition program, or any other known method of inputting electronic data. The display can include a computer, with an input interface and output interface such as a monitor and/or speakers.

In one embodiment, the display components 180 include a microprocessor and a memory. The memory can hold instructions for execution by the microprocessor, which cause the computer to perform the executed stages. In another embodiment, the display components include a hardware interface that is installed within one or more computers capable of running software for displaying the pressure drop on a screen.

The pressure-sensing device may be an accessory device that is separate from the catheter device to which it attaches in one embodiment. For example, turning to FIG. 1, the device 10 may include sensor components 160 and 162 for connecting to lumens 110 and 130 of an existing catheter 105 via ports in the lumens. This may facilitate use of an add-on device with existing catheters. In addition, this embodiment would potentially allow the pressure-sensing device to be used with a disposable catheter. For example, a single device (comprising sensors 160 and 162 and differential pressure circuitry 170) can mate with ports 161 and 163 of a disposable catheter.

The sensor components 160 and 162 can include pressure sensors in one embodiment, and also can also include connectors for attaching to the lumen ports. For example, in one embodiment, the sensor components may comprise additional tubing that connects to the ports and leads to differential pressure circuitry 170, where a pressure transducer makes the pressure reading. In one embodiment, the differential pressure circuit 170 and/or sensor components 160, 162 wirelessly transmit the pressure difference and/or sensed values to the output circuitry.

In another embodiment, the catheter includes the pressure-sensing components as a single pre-manufactured device. The catheter may already include pressure sensors within two separate lumen. However, this embodiment may still employ differential pressure circuitry and output circuitry that is maintained exterior from the patient, and kept in communication with the catheter through either conductive wires or a wireless technology. For example, the catheter may include a transmitter that transmits encrypted signals to a receiver kept external to the patient, the receiver being coupled to the differential pressure circuitry.

The above embodiments can be used with any elongate structure that delivers a balloon into a patient, including, but not limited to, any lumen, catheter, tool, tubing, pin or specialized medical device.

Figure 7:
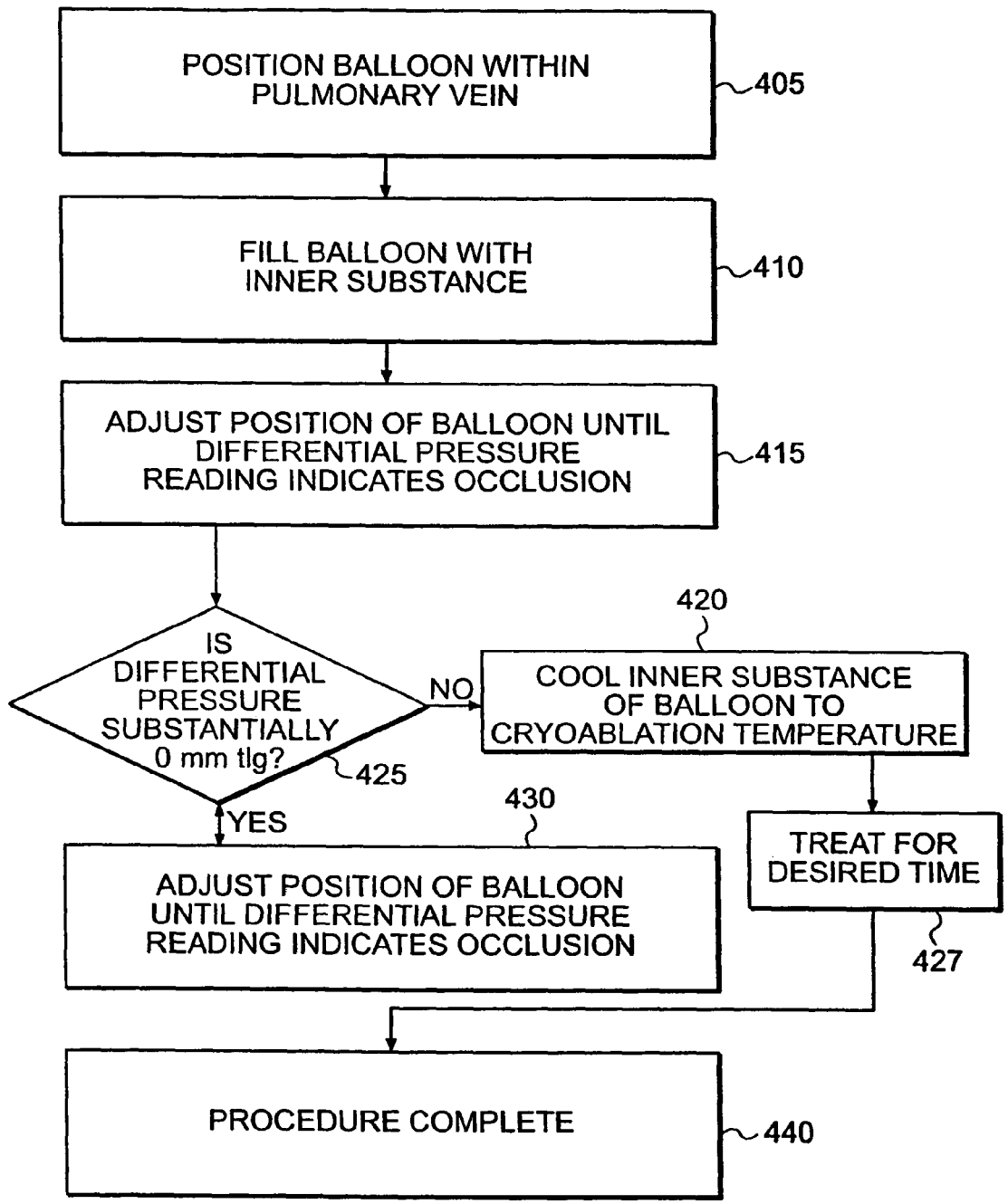
FIG. 7 is an exemplary flow chart including steps for performing a cryoablation procedure in accordance with one embodiment.

A method for using a medical device consistent with an embodiment herein has already been described, but for the sake of clarity, various exemplary stages of use are presented in an exemplary flow chart in FIG. 7. At stage 405, the expandable member 138, such as a balloon, is positioned within an anatomic passageway 148, such as the pulmonary vein. Positioning the balloon requires making at least one small incision in the patient, through which the balloon is fed. In one embodiment, the balloon is part of a catheter that is fed into the pulmonary vein from within smaller veins that connect to the pulmonary vein. A guide wire can be used to navigate the balloon into place. In some embodiments, a lens lumen or catheter-mounted camera eye, such as an endoscope, is used to effectively navigate the balloon into position. In other embodiments and procedures, the balloon can be placed by making an incision in proximity to the final destination of the balloon, and directly placing the balloon in position.

At stage 410, the balloon is inflated with an ablation fluid and/or an inflation fluid that can comprise one or more fluids including a cryo-fluid. In general, if the balloon is heated or cooled to perform the ablation, the ablation fluid can include at least the variety of known liquid and/or gas ablation fluids already discussed.

At stage 415, the position of the balloon and/or inflation of the balloon is adjusted until the pressure difference between the proximal and distal sides of the balloon falls within the range indicative of the desired degree of occlusion. In some embodiments, aural feedback is provided to the user. In another embodiment, the user monitors the pressure levels on a display to assure a satisfactory the pressure difference In some embodiments, positioning the balloon includes inflating the balloon and/or moving the balloon.

Positioning the balloon can include the process of stages 425 and 430, which can be iterative. Stage 425 includes checking whether the differential pressure is approximately zero mm Hg. This step can be performed through out the therapeutic procedure and/or ablation step to reduce the likelihood of incomplete occlusion. In another embodiment, the user monitors a visual display, such as a pressure versus time graph, to determine if the occlusion is no longer complete.

At stage 430, if a break in the occlusion seal is detected, the balloon is repositioned as in step 415 until the pressure difference varies in a range indicative of complete occlusion. As previously stated, for most patients, a complete occlusion of the pulmonary vein will result in a pressure difference in the range of about 30 mm Hg to about 40 mm Hg.

Once the balloon is positioned and occlusion is present, the cryoablation temperature is applied at stage 420. In one embodiment, this includes cooling the inner substance of the balloon to a temperature capable of killing tissue in contact with the balloon. In another embodiment, a separate cryoablation member is cooled to a level capable of destroying the tissue. Step 420 can include additional filling if the balloon (or other expandable member) was not completely filled in step 410 or if inner fluid is cycled through the balloon as a method of applying the temperature to the tissue. Similarly, step 420 may include filling a separate chamber with cryofluid (i.e., and ablation fluid) in one embodiment. Consequently, some embodiments perform step 420 simultaneously with step 410, while other embodiments do not.

At stage 427, the treatment continues for a desired amount of time. During this time, the pressure difference across the balloon can be monitored to ensure a uniform ablation. If the occlusion becomes incomplete during the process, the iterative process of stages 425 and 430 can be followed to regain a seal. The seal is maintained for a predetermined amount of time while heat is transferred from device 10 to the anatomic tissue or heat is transferred from the tissue to device 10. Once that predetermined amount of time has elapsed, the ablation procedure is completed at stage 440.

Although several embodiments refer to a balloon, the expandable member, as previously explained, is broader than just the balloon embodiment. Therefore, alternative embodiments exist for all embodiments using described herein as using a balloon. In the alternate embodiments, a different expandable member is used.

Other embodiments will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of performing an ablation procedure on a patient, comprising:
   determining a pressure threshold range for the patient;
   inserting a cryoablation catheter having an expandable member at least partially within an anatomic structure, the expandable member having a proximal surface and a distal surface;
   expanding the expandable member and contacting the anatomic structure at a contact area;
   measuring a pressure difference between a first location proximal to the contact area and a second location distal to the contact area;
   adjusting a seal between the cryoablation catheter and the contact area till the measured pressure difference is within the predetermined threshold range indicating a complete occlusion of the anatomic structure:
   continuously monitoring the pressure difference during the ablation procedure;
   readjusting the seal between the cryoablation catheter and the contact area to maintain the pressure difference in the threshold range; and
   providing an aural indication when the pressure difference drops below the threshold range, wherein providing the aural indication includes setting a time offset between the pressure drop below the threshold range and the aural indication.

2. The method of claim 1, wherein the anatomic structure is a pulmonary vein.

3. The method of claim 2, wherein the pressure difference is measured between the pulmonary vein and the atrium.

4. The method of claim 2, wherein the pulmonary vein is completely occluded if the measured pressure difference is within the threshold range of about 10 mm Hg and 50 mm Hg.

5. The method of claim 1, further comprising:
   ablating tissue if the pressure difference is within the threshold range.

6. The method of claim 5, wherein the method further comprises:
   stopping ablating tissue if the pressure difference drops below the threshold range.

7. The method of claim 1, wherein the pressure distal to the contact area is sensed inside a proximal portion of a lumen that has an open distal end and a closed proximal end, the open distal end positioned distal to the contact area.

8. The method of claim 1, wherein measuring the pressure difference comprises detecting the pressure distal to the contact area through a first lumen and detecting the pressure proximal to the contact area through a second lumen.

9. The method of claim 1, further comprising displaying pressure difference on a screen.

10. The method of claim 9, further comprising charting the pressure difference with respect to time.

11. The method of claim 1, wherein adjusting the seal comprises repositioning the cryoablation catheter within the anatomic structure.

12. The method of claim 1, wherein adjusting the seal comprises adjusting a pressure within the expandable member.

13. The method of claim 1, further comprising a step of providing an aural indication when the pressure difference reaches the threshold range.

14. A method of performing an ablation procedure on a patient, comprising:
   determining a pressure threshold range for the patient;
   inserting a cryoablation catheter having an expandable member at least partially within an anatomic structure, the expandable member having a proximal surface and a distal surface;
   expanding the expandable member and contacting the anatomic structure at a contact area;
   measuring a pressure difference between a first location proximal to the contact area and a second location distal to the contact area;
   adjusting a seal between the cryoablation catheter and the contact area till the measured pressure difference is within a predetermined threshold range;
   providing an aural indication when the measured pressure difference is within the predetermined range; and providing an aural indication when the measured pressure difference drops below the threshold range, wherein providing the aural indication includes setting a time offset between the pressure drop below the threshold range and the aural indication.

15. The method of claim 14, further comprising displaying the pressure difference on a screen.

16. The method of claim 14, further comprising a step of continuously monitoring the pressure difference during the ablation procedure.

17. The method of claim 14, further comprising a step of readjusting the seal between the cryoablation catheter and the contact area to maintain the pressure difference in the threshold range.

18. A method of performing an ablation procedure on a patient, comprising:
 determining a pressure threshold range for the patient;
 inserting a cryoablation catheter having an expandable member at least partially within an anatomic structure, the expandable member having a proximal surface and a distal surface;
 expanding the expandable member and contacting the anatomic structure at a contact area;
 measuring a pressure difference between a first location proximal to the contact area and a second location distal to the contact area;
 adjusting a seal between the cryoablation catheter and the contact area till the measured pressure difference is within a predetermined threshold range;
 continuously monitoring the pressure difference during the ablation procedure;
 providing an aural indication during the ablation procedure when the measured pressure difference drops below the predetermined threshold range to alert a physician about a break in the seal, wherein providing the aural indication includes setting a time offset between the pressure drop below the threshold range and the aural indication; and
 readjusting the seal between the cryoablation catheter and the contact area to maintain the pressure difference in the threshold range.

19. The method of claim 18, further comprising providing an aural indication when the measured pressure difference is within the predetermined range.

20. The method of claim 18, wherein the pressure distal to the contact area is sensed inside a proximal portion of a lumen that has an open distal end and a closed proximal end, the open distal end positioned distal to the contact area.

21. The method of claim 18, wherein measuring the pressure difference comprises detecting the pressure distal to the contact area through a first lumen and detecting the pressure proximal to the contact area through a second lumen.

22. The method of claim 18, wherein adjusting the seal comprises repositioning the cryoablation catheter within the anatomic structure.

23. The method of claim 18, wherein adjusting the seal comprises adjusting a pressure within the expandable member.

24. The method of claim 18, further comprising charting the pressure difference with respect to time.

* * * * *